United States Patent [19]

Nuzzo

[11] Patent Number: 5,523,236
[45] Date of Patent: Jun. 4, 1996

[54] CLOSURE ASSEMBLY FOR CELL CULTURE VESSELS

[75] Inventor: Michael J. Nuzzo, Newark, N.J.

[73] Assignee: Becton, Dickinson and Company, Franklin Lakes, N.J.

[21] Appl. No.: 292,635

[22] Filed: Aug. 18, 1994

[51] Int. Cl.⁶ .................................................. C12M 1/00
[52] U.S. Cl. ..................... 435/304.1; 215/236; 215/237; 215/261; 215/307; 215/308; 215/329; 220/360; 220/361; 220/367.1; 220/371; 220/373
[58] Field of Search .................................. 215/235, 236, 215/237, 245, 261, 307, 308, 329; 220/360, 361, 367.1, 373, 371; 435/288.1, 304.1

[56] References Cited

U.S. PATENT DOCUMENTS

| | | | |
|---|---|---|---|
| 2,950,833 | 8/1960 | Short. | |
| 3,326,401 | 10/1965 | De Long | 435/304.1 |
| 4,327,842 | 5/1982 | Walter | 220/367 |
| 4,377,247 | 3/1983 | Hazard et al. | 222/517 |
| 4,437,574 | 3/1984 | Ruklic | 215/247 |
| 5,047,347 | 9/1991 | Cline | 435/296 |
| 5,339,993 | 8/1994 | Groya et al. | 222/153 |
| 5,391,496 | 2/1995 | Kayal et al. | 435/286 |
| 5,395,006 | 3/1995 | Verma | 220/371 |

*Primary Examiner*—David A. Redding
*Attorney, Agent, or Firm*—Arthur D. Dawson

[57] ABSTRACT

A closure for providing selective access to and for closing a cell culture vessel includes an open cylindrical first portion for attaching the closure to the cell culture vessel. The first portion includes a passageway for access to the vessel. The closure includes a second portion attached to the first portion by a hinge for closing the access passageway. The second portion additionally includes a vent which has a porous membrane covering it to prevent passage of microorganisms through the vent. The closure includes a third portion which is attached by a hinge to the second portion for closing the vent. Either the vent or the access passageway may be opened with one hand providing easy access and selective closure of the cell culture vessel.

11 Claims, 6 Drawing Sheets

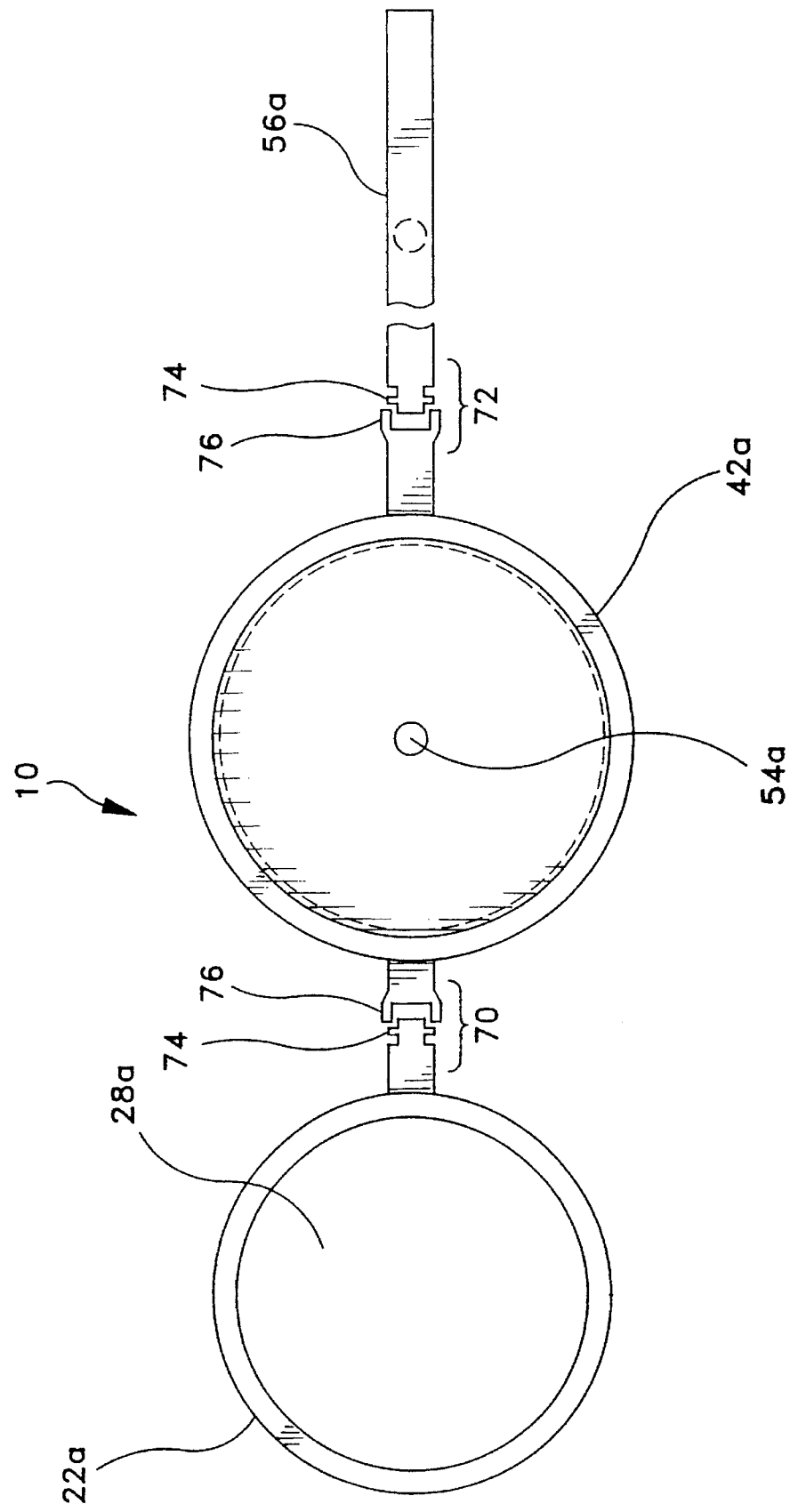

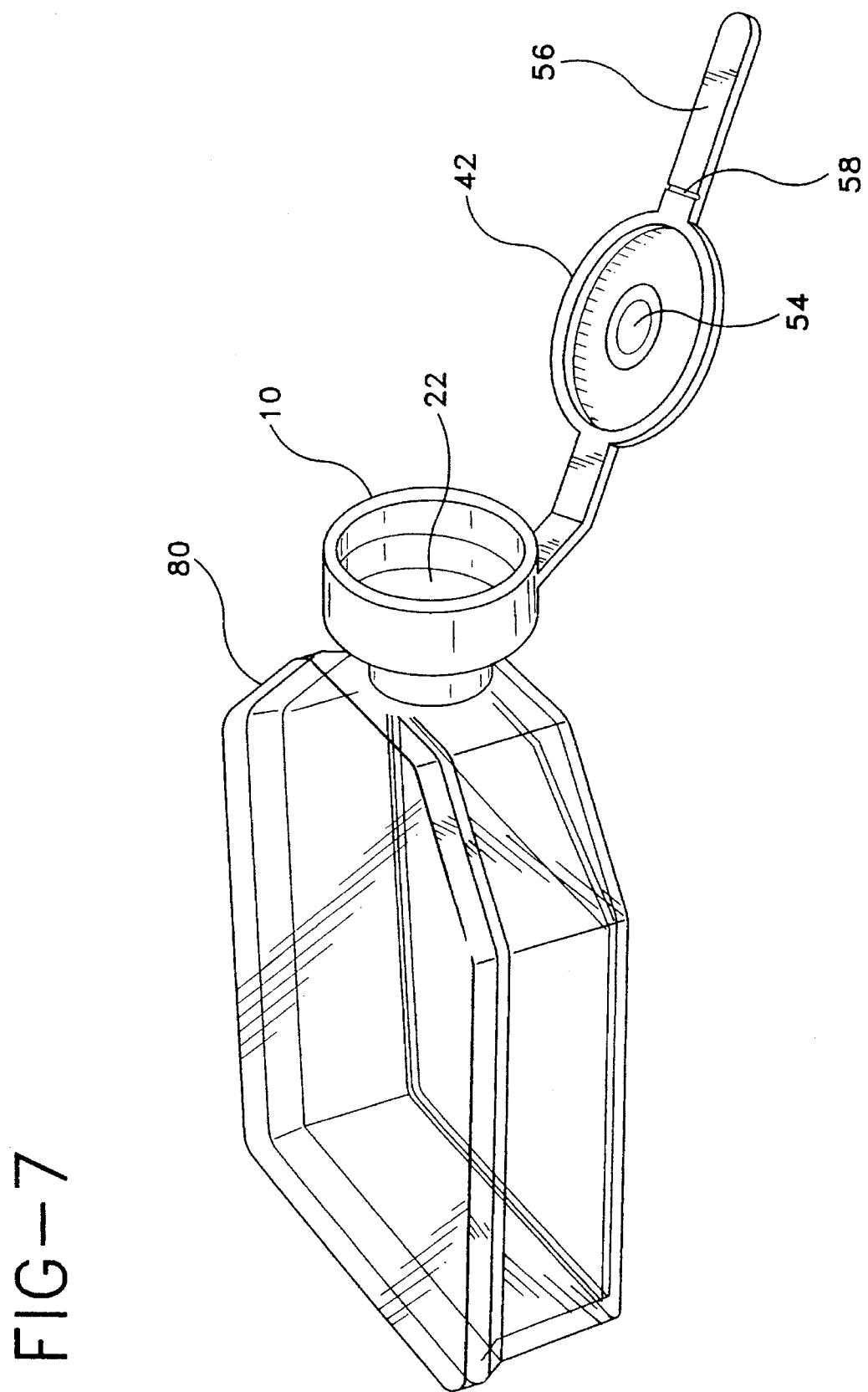

CLOSURE ASSEMBLY FOR CELL CULTURE VESSELS

FIELD OF THE INVENTION

This invention relates to a closure assembly for cell culture vessels and more particularly to a closure assembly which provides selective venting and access to the vessel with secure closure.

BACKGROUND OF THE INVENTION

Culturing of cells of various types has become a routine process in many laboratories. Tissue culture is conducted on scales ranging from multiwell microplates involving only a few cells to large reactors having billions of cells.

There are several types of vessels used in laboratory settings for size scale-ups or cell culturing systems. These vessels are stationary flasks and roller bottles. The vessels are charged with growth media, seeded with cells and placed in incubation chambers with suitable environments for the particular cells being grown, which may include an atmosphere altered from ambient air. Additionally, in many culture systems there is a need to allow the vessel to vent gas emitted by the cultured cells so that it may equilibrate with the chamber atmosphere.

The need to allow equilibration between the vessel and the chamber is addressed in several ways. Since many vessels have necks with screw caps, one solution is simply to leave the caps ajar which allows gas interchange. While this technique allows gas interchange, it may also allow microbial contamination of the culture system.

The need for gas exchange between culture vessels and incubation chamber atmosphere was recognized in U.S. Pat. No. 5,047,347 which discloses a gas impermeable culture flask with provisions for gas permeation. The disclosure includes a cap for a vessel including a gas permeable insert and a hinged cover to close the gas cap for a vessel including a gas permeable insert and a hinged cover to close the gas permeable insert. The disclosure also includes a culture vessel with a sidewall port having a gas permeable insert having a cover. Vessels incorporating the teaching of U.S. Pat. No. 5,047,347 with a side port are complex to manufacture and thus are not widely used. Vessels with caps following the teachings of this patent may be of standard design, but the caps must be removed for access to the contents, an operation which may disturb the growing cells.

As cell culture programs are scaled up, a laboratory may conduct multiple vessels of a particular culture. These cultures may require periodic removal or changing of the fluids in the vessel on a regular basis. If a cell culture vessel closure system were available which included provisions for venting, closure and one handed operation, the time for the transfers and the amount of disruption to the growing cells would be minimized. The present invention is such a closure device.

SUMMARY OF THE INVENTION

A closure for providing selective access to and for closing a cell culture vessel includes an open cylindrical first portion having a top and a bottom with a passageway therethrough. The passageway serves to provide access to the cell culture vessel. The first portion has an outside surface and an inside surface. The inside surface has female locking elements for accepting a neck of a cell culture vessel and forming a sealing attachment with the conjugate male elements on the neck. The closure further includes a second portion having a hinged attachment to the first portion. The second portion has an open position where the passageway in the first portion is not obstructed and a closed position where the passageway is obstructed. The second portion has a top surface and a bottom surface with respect to the open position. The top surface has a raised member sized to fit within the passageway in the first portion and selectively retain the second portion in the closed position. The second portion further includes an area defined by the raised member with an open vent from the top surface to the bottom surface so that when the second portion is in the closed position a gas interchange may occur between the atmosphere within and without the vessel through the vent. The closure further includes a third portion attached to the second portion by a hinge the third portion has an upper surface with respect to an open position and a lower surface with a plug projecting therefrom for occluding the vent at the bottom of second portion when the third portion is in the closed position.

Preferably, the vent in the second portion has a gas permeable membrane bonded over the top surface of the second portion to prevent entrance of microorganisms from entering the vent.

Preferably, the inside surface of the neck has female threads to match male threads on the neck of the culture vessel.

The hinged attachments preferably are living hinges formed by molding the first part, the second part and the third part as a unitary structure formed by injection molding in a single step from a thermoplastic resin such as polypropylene, polyethylene and copolymers of polyethylene and polypropylene.

The closure for a cell culture vessel of the present invention may be selectively opened and closed with one hand. It provides rapid access to the contents of a cell culture vessel with a wash bottle or pipette. Additionally, the closure allows selective controlled venting and tight sealing by opening and closing. It can be easily and economically manufactured, facilitating the use of cell culture as a synthesis technique.

BRIEF DESCRIPTION OF THE DRAWINGS

FIG. 6 is an exploded top plan view of an alternate embodiment of the closure of the present invention wherein its portions are separate; and FIG. 7 is a perspective view of a closure of the present invention in use on a flask type cell culture vessel.

DETAILED DESCRIPTION OF THE INVENTION

Figure 1:
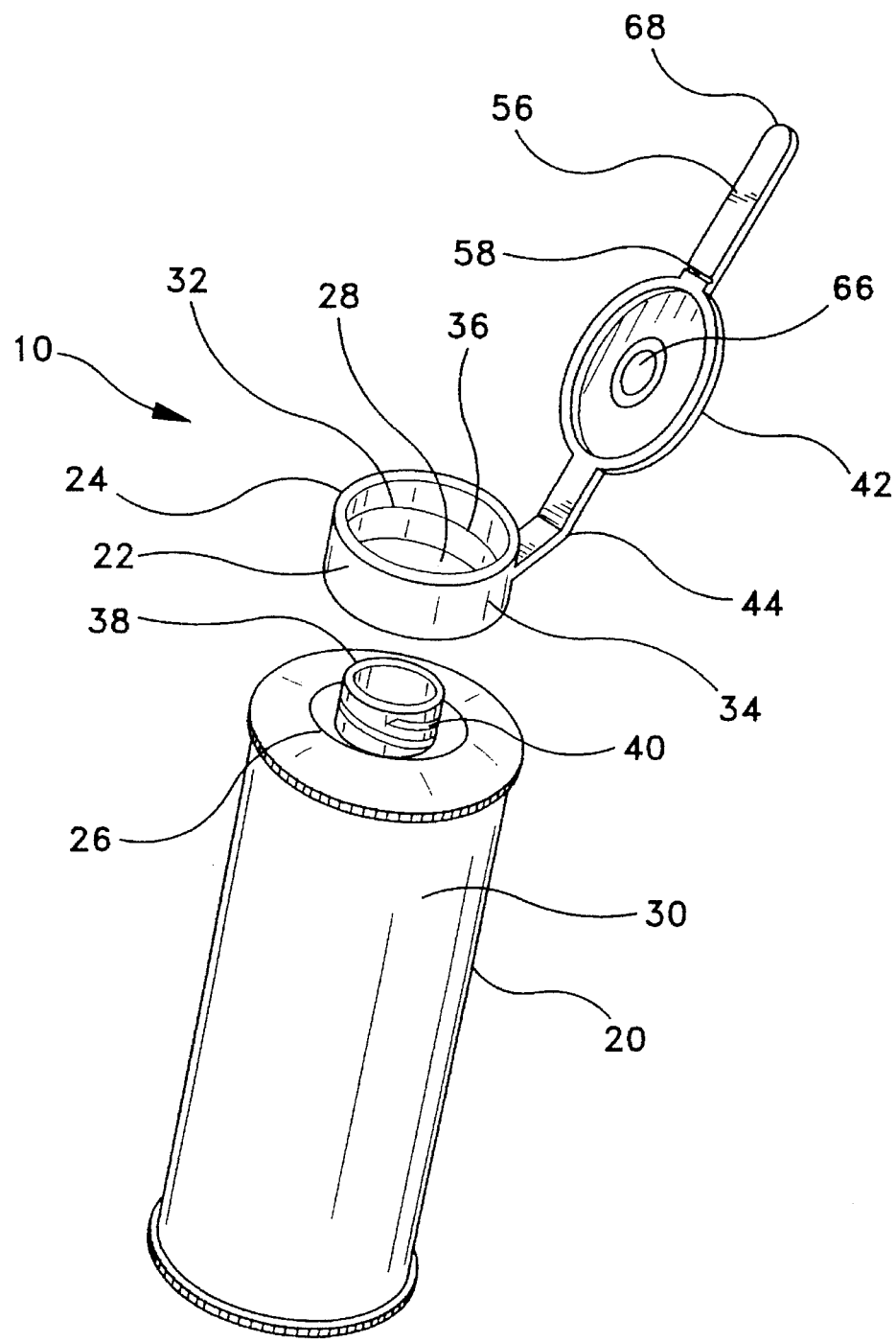
FIG. 1 is an exploded perspective view of the preferred closure of the present invention mounted on a standard laboratory cell culture roller bottle with the closure in the open position.

While this invention is satisfied by embodiments in many different forms, there is shown in the drawings and will herein be described, several embodiments of the invention with the understanding that the present disclosure is to be considered as exemplary of the principles of the present invention and is not intended to limit the scope of the invention to the embodiments illustrated. The scope of the invention will be measured by the appended claims and their equivalents.

As shown in FIGS. 1–5, a closure 10 for providing selective access to and for closing a cell culture vessel 20 includes an open cylindrical first portion 22 having a top 24 and a bottom 26 with a passageway 28 therethrough. Passageway 28 provides access to an interior 30 of cell culture vessel 20. First portion 22 has an inside surface 32 and an outside surface 34. Inside surface 32 preferably has female locking elements 36 for accepting conjugate male locking elements 40 on fleck 38 of the vessel.

Figure 2:
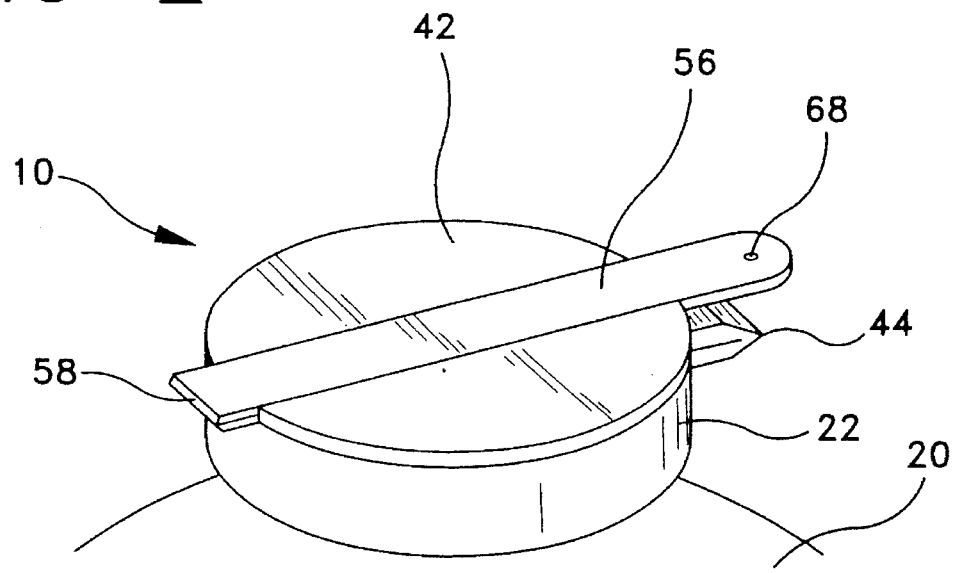
FIG. 2 is a perspective view of the closure of FIG. 1 in the fully closed position.
Figure 3:
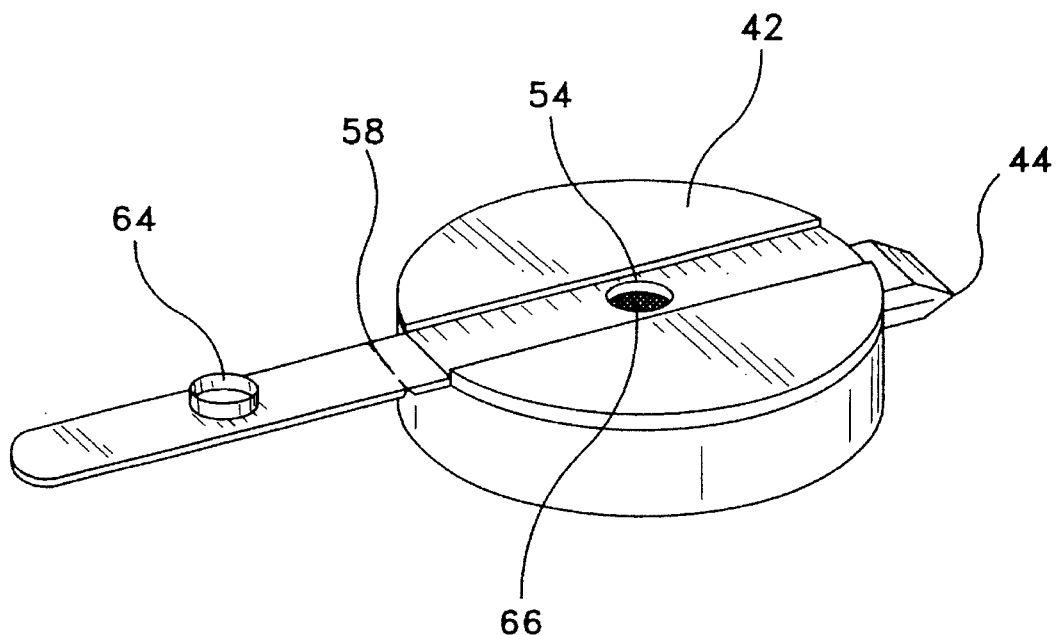
FIG. 3 is a perspective view of the closure of FIG. 1 with the vent open.

Closure 10 further includes a second portion 42 which preferably has a hinged attachment 44 to first portion 22. As shown in FIG. 1, closure 10 has an open position where passageway 28 in first portion 22 is not obstructed and a closed position as shown in FIGS. 2 and 3, where passageway 28 is obstructed. Second portion 42 has a top surface 46 and a bottom surface 48 with respect to the open position. Top surface 46 has a raised member 50 having an outside diameter A which preferably fits with an interference inside an inside diameter B in passageway 28 to retain selectively second portion 42 in the closed position shown in FIGS. 2 and 3. Second portion 42 further includes an area 52 within raised member 50 with an open vent 54 from top surface 46 to bottom surface 48 so that when second portion 42 is in the dosed position as shown in FIG. 3, a gas interchange may occur through vent 54 between an atmosphere within the vessel and the outside environment.

Closure 10 preferably includes a third portion 56 with a hinged attachment 58 to second portion 42. Third portion 56 has an upper surface 60 and a lower surface 62. Lower surface 62 preferably has a circular plug 64 projecting therefrom. Plug 64 has an outside diameter E sized to fit within an inside diameter F of vent 54 and occlude vent 54 when portion 56 is in the closed position as shown in FIG. 2.

Preferably, vent 54 has a gas permeable membrane 66 bonded to surface 56 for substantially preventing passage of microorganisms through vent 54 while allowing gas interchange. Since most cell culture vessel necks 38 have male threads 40 as locking elements, preferably female locking elements 36 are mating threads which allow closure 10 to be mounted and form a sealing attachment on a cell culture vessel. It is intended that the closure of the present invention may also be provided with female locking elements such as snap-fit, bayonet fit, twist-lock or the like to allow the present closure to be mounted on other types of culture vessels, should vessels with these type of closures be employed. The closure should form a substantially fluid tight seal with the vessel neck.

Closure 10 preferably is formed from a thermoplastic resin such as, but not limited to, polypropylene, polyethylene or copolymers of polyethylene and polypropylene. In the art of injection molding it is known that if an article formed of certain polymers, including those listed above, has an area of reduced thickness relative to other portions of the article, a living hinge can be formed by flexing the article at the area of reduced thickness after it has been freshly removed from the molding tool. The immediate flexion of the article at the area of reduced thickness serves to orient the molecules within the flex area and allow the article to then be repeatedly flexed at the area of reduced thickness with no degradation of properties. If the article is not flexed when it is freshly removed from the mold, the ability to form the hinge at the area of reduced thickness is lost because the molecules will not be oriented as the article is flexed. Hence the name "living hinge." Polyethylene, polypropylene and copolymers of polyethylene and polypropylene are particularly well suited for the formation of a living hinge but any other thermoplastic resin which forms a living hinge may be used for particular applications.

Preferably hinged attachments 44 and 58 are areas of reduced thickness relative to the thickness of closure 10 and preferably closure 10 is flexed at area of reduced thickness 44 and 58 when closure 10 is freshly removed from the mold thereby forming the living hinge at attachment points 44 and 58.

Figure 4:
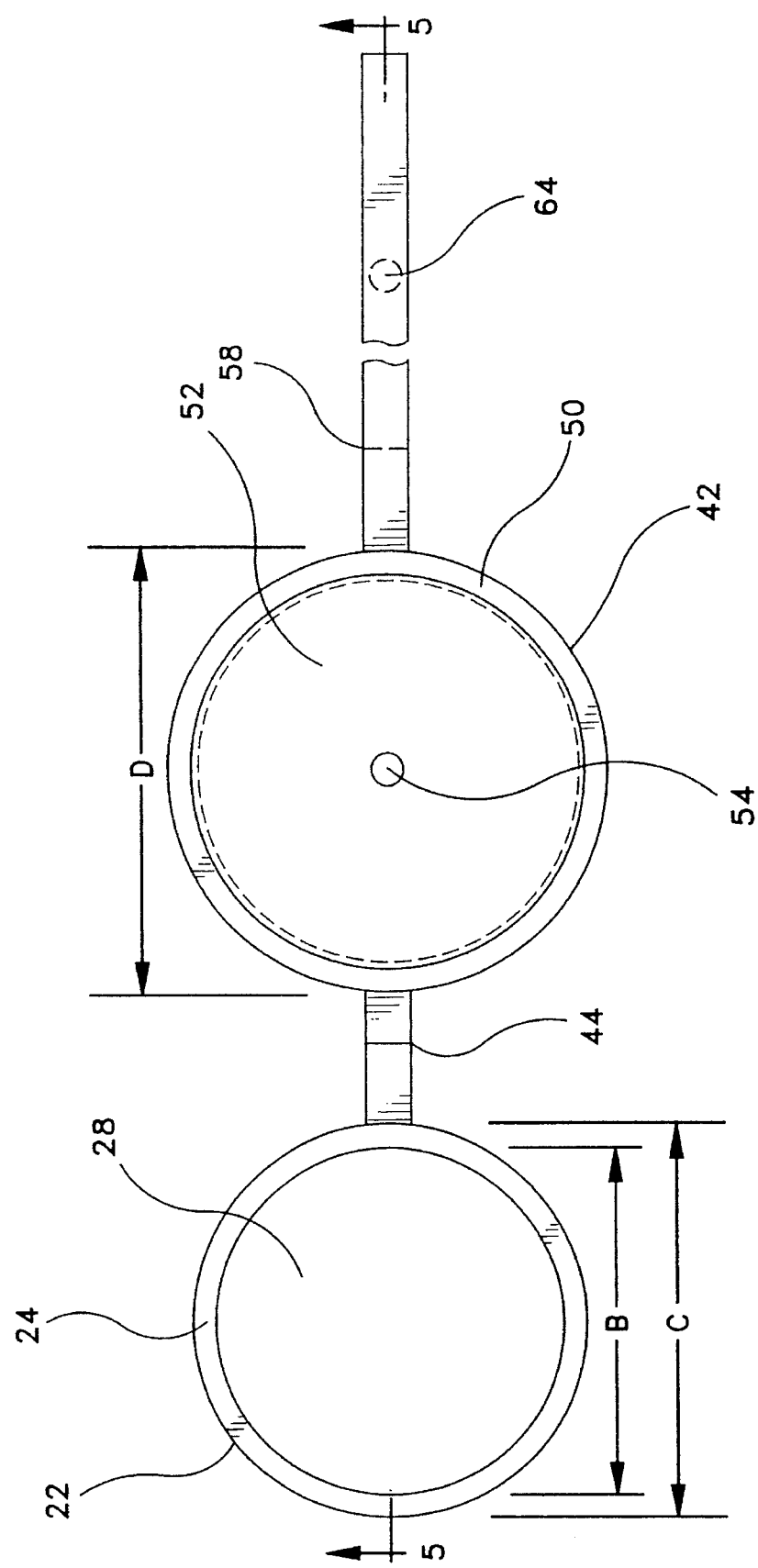
FIG. 4 is a top plan view of the closure of FIG. 1 in the fully opened position.
Figure 5:
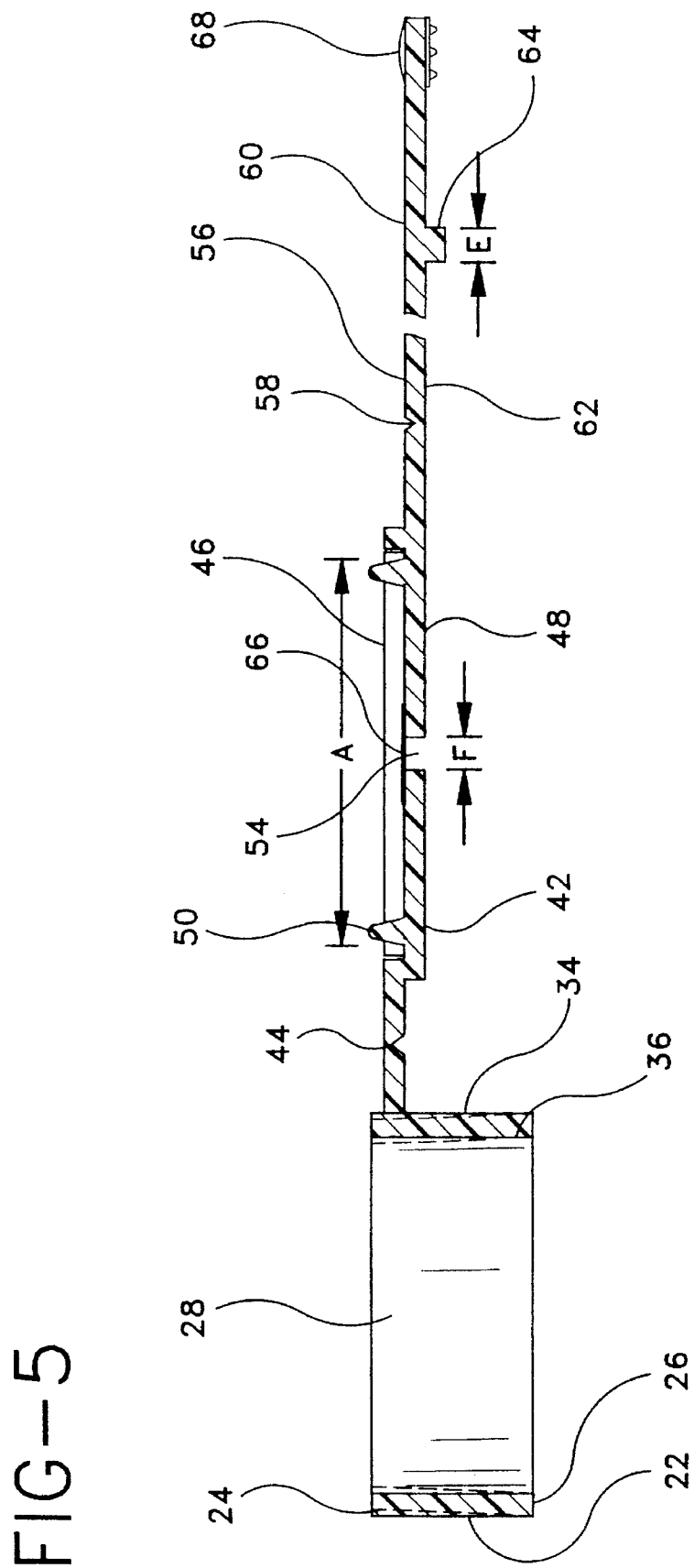
FIG. 5 is a cross sectional view of the closure of FIG. 1 in the fully opened position.

Referring to FIGS. 4 and 5, second portion 42 preferably fits with an interference onto first portion 22. Raised member 50 has an outside diameter A and first passageway 28 has inside diameter B. When diameter A is greater than diameter B by about 0.001 to about 0.01 inches, an interference fit will exist when second portion 42 is in the closed position. Preferably raised member 50 is continuous and circular thereby closing passageway 28 when second portion 42 is in the closed position. An alternate preferred embodiment for the relationship between first potion 22 and second portion 42 in the closed position would be the case where an inside diameter D of raised portion 50 is greater than an outside diameter C of first portion top surface 24. Preferably top surface 24 is circular. When D is larger than C and second portion 42 is in the closed position, second portion raised member 50 fits over outside top surface 24 thereby forming a cap and obstructing passageway 28.

Preferably vent 54 is a porous membrane with a pore size between about 0.01 microns to about 0.2 microns which allows an exchange of gases between the inside of the culture vessel and the chamber, but substantially prevents the transmission of microorganisms through the membrane. Suitable gas-permeable materials having suitable pore size for allowing the desired gas exchange while substantially preventing the passage of microorganisms include but are not limited to Celgard™(Hoechst-Celanese), Nuclepore ™(Nuclepore Corp.) and Millipore GS™(Millipore Corp.). It is preferred that any material used for the vent material be easily attached to the closure material and not be water soluble or capable of supporting microbial growth.

Preferably hinged attachment 58 joining second portion 42 to third portion 56 projects outwardly beyond outside surface 34 of the first portion allowing hinged attachment 58 and be used to facilitate opening and closing second portion 42. It is further preferred that third portion 56 have a projection 68 beyond surface 34 when third portion 56 is in the closed position thus facilitating opening and closing of third portion 56 and vent 54. Preferably the locations of hinged attachment 58 and hinged attachment 44 are diametrically opposed on second portion 42 so that when the second potion and the third portion are in the open position, first portion 22, second portion 42 and third portion 56 are generally linearly arrayed, but for particular applications, attachments 58 and 44 may have other relationships around second portion 42.

An alternative embodiment to the closure of the present invention is shown in Fig. 6. In this alternate embodiment which may be preferred for particular applications, there are elements similar in structure and function to the closure of the present invention as shown in FIGS. 1–5. Accordingly, substantially similar components that perform substantially similar functions are numbered identically to those of embodiment of FIGS. 1–5 except that the suffix "a" is used to identify those components in FIG. 6.

As shown in FIG. 6, a closure 10a for providing selective access to and for closing a cell culture vessel includes an open cylindrical first portion 22a with a passageway 28a therethrough. Passageway 28a provides access to the cell culture vessel. Closure 10a further includes a second portion 42a which has a hinged attachment 70 to first portion 22a. Closure 10a also includes a third portion 56a joined to second portion 42a by a hinged attachment 72. All functions and structures as shown in FIGS. 1–5 are substantially duplicated by the embodiment of FIG. 6, with the exceptions that portions 22a, 42a and 56a are individually formed as separate items and are hingedly attached by hinges 70 and 72 respectively having rotatable mechanical joints. The joints 70 and 72 illustrated are of the pin and socket type having each having a pair of projections 74 to fit with yokes 76 with a socket. The actual form of the mechanical hinge is not critical to the invention; any simple hinge having a rotatable joint fulfills the requirements.

The embodiment of FIG. 6 allows the interchange of first portions having fittings to accommodate different size culture vessels or vessels with a different neck configuration. Additionally, it is envisioned that the closure of the present invention may be manufactured with one mechanical hinge joining the first portion and the second portion while the second and third portions be joined by a living hinge to simplify the manufacture.

The applicability of a closure to culture vessels other than the roller bottle 20 as shown in FIG. 1 is shown in FIG. 7 where closure 10 is mounted on a flat flask type vessel 80.

The closure of the present invention with second portion 42 in the open position allows substantially unimpeded access to the cell culture vessel. The closure may be opened and closed with one hand minimizing handling. Since it is still attached when opened, this closure substantially eliminates cross contamination when handling multiple bottles. The present closure further allows for venting the vessel during incubation and for substantially closing the vessel during transfers to maintain a desired atmosphere over the contents of the vessel.

What is claimed is:

1. A closure for providing selective access to and for closing a cell culture vessel comprising:

An open cylindrical first portion having a top and a bottom with a passageway therethrough, said passageway providing access to an interior of a culture vessel, said first portion having an outside surface and an inside surface, said inside surface having female locking elements for accepting a neck of the cell culture vessel and for forming a sealing attachment with conjugate male locking elements on the neck of the vessel;

a second portion having a hinged attachment to said first portion, said second portion having an open position wherein said passageway in said first portion is not obstructed and a closed position wherein said passageway in said first portion is obstructed, said second portion having a top surface and a bottom surface, with respect to said open position, said top surface having a raised member sized to fit within said passageway in said first portion and selectively retain said second portion in said closed position, said second portion further including an area defined by said raised member having an open vent from said top surface to said bottom surface including a gas permeable membrane bonded thereover on said top surface so that when said second portion is in said closed position a gas interchange may occur through said vent between an atmosphere within said vessel and without said vessel; and a third portion having a hinged attachment to said second portion, said third portion having an upper surface with respect to an open position and a lower surface, said lower surface having a plug projecting therefrom for occluding said vent in said second portion, said third portion having a closed position wherein said plug occludes said vent at said second portion bottom surface and said open position wherein said vent is open.

2. The closure of claim 1 wherein said gas permeable membrane is a porous membrane having a pore size between about 0.01 microns to about 0.2 microns thereby allowing said gas interchange through said vent while substantially preventing the passage therethrough of microorganisms.

3. The closure of claim 1 wherein said female locking elements comprise threads.

4. The closure of claim 1 wherein said hinged attachment between said first portion and said second portion and said hinged attachment between said second portion and said third portion comprise living hinges, said closure being a unitary article of manufacture.

5. The closure of claim 4 wherein said first portion, said second portion and said third portion are formed as said unitary article of manufacture by an injection molding process in a mold tool from a thermoplastic resin selected from the group consisting of polyethylene, polypropylene and copolymers of polyethylene and polypropylene.

6. The closure of claim 1 wherein said passageway in said first portion is cylindrical having an inside diameter and said raised member is continuous and circular having an outside diameter sized to fit with an interference fit within said passageway when said second portion is in said closed position so that said passageway is obstructed and to retain releasably said cap in said closed position.

7. The closure of claim 1 wherein said hinged attachment between second portion and said third portion forms an extended tab when said second portion is in said closed position and said third portion is in said closed position, said tab serving to facilitate moving said second portion from said closed position wherein said passageway is obstructed to said open position thereby providing free access to said passageway into said vessel.

8. The closure of claim 1 wherein said first portion outside surface is circular having an outside diameter and said raised member is circular and continuous having an inside diameter larger than said first portion outside diameter so that when said second portion is in said closed position, said second portion raised member fits outside said first portion with an interference fit thereby forming a cap and selectively obstructing said passageway.

9. The closure of claim 1 wherein said first portion, said second portion and said third portion are individually formed by an injection molding process and said hinged attachments comprise hinges having rotatable mechanical joints.

10. The closure of claim 1 wherein said third portion includes an extension portion so that when said second portion and said third portion are in said closed positions, said extension portion extends beyond said first portion and said second portion, said extension portion serving to facilitate moving said third portion from said closed position to said open position.

11. The closure of claim 1 wherein said hinged attachment between said first portion and said second portion and said hinged attachment between said second portion and said third portion are diametrically opposed on said second portion so that when said second portion and said third portion are in said open position, said first portion, said second portion and said third portion are linearly arrayed.

* * * * *